(12) United States Patent
Winsor (10) Patent No.: US 10,117,575 B2
(45) Date of Patent: Nov. 6, 2018

(54) METHOD AND APPARATUS FOR FIXATION MEASUREMENT (71) Applicant: REBIScan, Inc., Cambridge, MA (US)

(72) Inventor: Robert Scott Winsor, Round Hill, VA (US)

(73) Assignee: REBISCAN, INC., Cambridge, MA (US)

( * ) Notice: Subject to any disclaimer, the term of this patent is extended or adjusted under 35 U.S.C. 154(b) by 214 days.

(21) Appl. No.: 14/806,593

(22) Filed: Jul. 22, 2015

(65) Prior Publication Data

US 2016/0022138 A1 Jan. 28, 2016

Related U.S. Application Data (60) Provisional application No. 62/028,348, filed on Jul. 24, 2014.

(51) Int. Cl.
A61B 3/14 (2006.01)
A61B 3/113 (2006.01)
G02B 26/10 (2006.01)
G02B 27/42 (2006.01)
G02B 19/00 (2006.01)
G02B 27/28 (2006.01)
A61B 3/00 (2006.01)

(52) U.S. Cl.
CPC .......... *A61B 3/113* (2013.01); *G02B 19/0028* (2013.01); *G02B 26/105* (2013.01); *G02B 26/106* (2013.01); *G02B 27/4233* (2013.01); *A61B 3/0025* (2013.01); *G02B 27/283* (2013.01)

(58) Field of Classification Search
CPC ....... A61B 3/113; A61B 3/0025; A61B 3/102; G01B 9/02091; G01B 2290/65; G01N 21/21; G06F 3/013; G02B 19/0028; G02B 26/105; G02B 26/107; G02B 27/4233; G02B 27/283
USPC ........................................ 351/206, 210, 246
See application file for complete search history.

(56) References Cited

U.S. PATENT DOCUMENTS

| 6,027,216 A | 2/2000 | Guyton et al. |
| 6,149,589 A | 11/2000 | Diaconu et al. |
| 2007/0002277 A1 | 1/2007 | Hanebuchi |
| 2010/0046953 A1* | 2/2010 | Shaw ...................... H01S 5/423 398/115 |
| 2010/0118132 A1 | 5/2010 | Yumikake et al. |
| 2011/0116045 A1 | 5/2011 | Utagawa |
| 2014/0160431 A1* | 6/2014 | Izatt ...................... A61B 3/102 351/206 |

(Continued)

OTHER PUBLICATIONS

International Search Report and Written Opinion cited in corresponding International Application No. PCT/US2015/041627 dated Oct. 15, 2015.

*Primary Examiner* — Collin X Beatty
(74) *Attorney, Agent, or Firm* — Amardeep S. Grewal; Reed Smith LLP (57) ABSTRACT A method and apparatus for fixation measurement includes rotating a first reflector comprising a diffraction component about a rotation axis, the first reflector being configured to reflect light received from a light source onto a second reflector via the diffraction component and reflect light received from the second reflector via the diffraction component and capturing light which is reflected by the second reflector and subsequently reflected by the first reflector with one or more photodetectors.

20 Claims, 11 Drawing Sheets (56) References Cited

U.S. PATENT DOCUMENTS

2016/0081547 A1\* 3/2016 Gramatikov ....... G06K 9/00604
351/210

\* cited by examiner

METHOD AND APPARATUS FOR FIXATION MEASUREMENT

RELATED APPLICATION DATA

This application claims priority to U.S. Provisional Application No. 62/028,348, filed Jul. 24, 2014, the disclosure of which is hereby incorporated by reference in its entirety.

BACKGROUND

There are various devices and methods used to assess the direction of fixation of an eye. One example of a fixation measurement device is described in U.S. Pat. No. 6,027,216 ("the '216 patent"), the contents of which are hereby incorporated by reference in their entirety.

In general, the device in the '216 patent assesses the direction of fixation by: (1) directing incident light to illuminate the fundus of the eye; (2) detecting light reflected from the fundus; (3) determining polarization-related changes between the incident light and the reflected light; and (4) correlating the polarization-related changes with changes known to occur with known fixation states of the eye.

Figure 1:
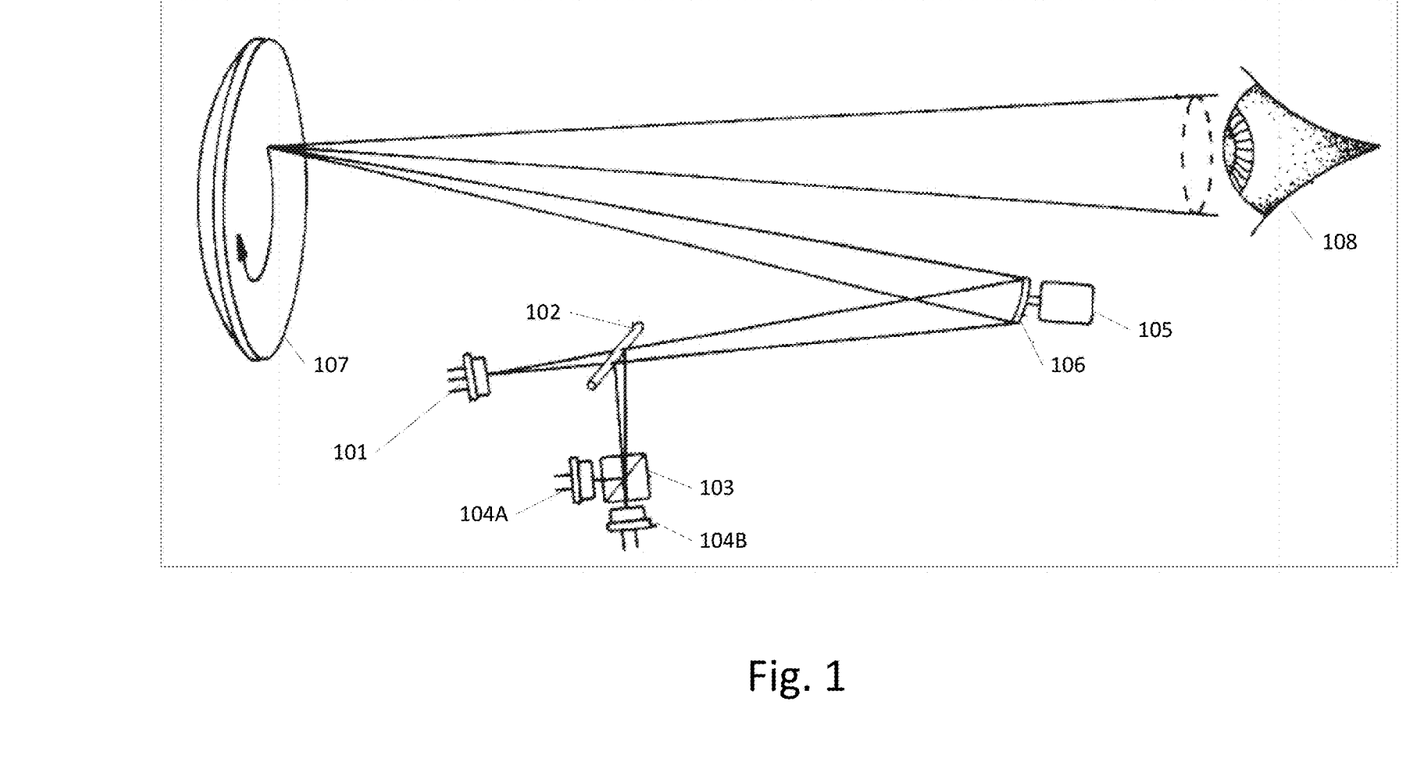
FIG. 1 illustrates a device for assessing the direction of fixation of an eye.

The '216 patent discloses devices which utilize a continuous scan of retinal areas to assess the direction of fixation of the eye. One example of such a device is shown in FIG. 1. The device includes a light source 101, a beam splitter 102, a polarization beam splitter 103, photodetectors 104A and 104B, a motor 105 having a rotatable shaft, a first concave mirror 106, and a second concave mirror 107.

The light source 101 provides a diverging beam of polarized light which passes through beam splitter 102 and is incident on the first concave mirror 106. The first concave mirror 106 is mounted in a tilted fashion on the shaft of the motor 105 such that the first concave mirror wobbles 106 slightly when the shaft rotates. The first concave mirror 106 forms an image of the light source 101 on the surface of the second concave mirror 107. The second concave mirror 107 is stationary and is larger than the first concave mirror 106. As the shaft of motor 105 rotates, the image of the light source 101 on the surface of second concave mirror 107 is continuously scanned about a circular path. The curvature of stationary second concave mirror 107 can be chosen such that an image reflected from the spinning first concave mirror 106 is formed directly at the eye 108. All the light leaving the spinning first concave mirror 106 is imaged by stationary second concave mirror 107 to pass through a stationary exit pupil of the device, designated by the dashed circle, which overfills the pupil of the eye 108. The eye 108 sees the spinning image of the light source 101 in the form of a circle of light on the surface of stationary second concave mirror 107. A continuous annular scan of retinal areas is thus achieved by the light incident on the eye 108.

In order to allow for rapid measurements of the light reflected from the fundus, it is desirable to operate the above-described scanning at a scanning rate of at least 100 Hz and preferably at rates of 200 Hz or more. Scan rates at 200 Hz or more permit measurements to be obtained when working with subjects that may be less than fully cooperative, as is commonly the case with very young children. Such rates require the mechanical rotation of the first concave mirror 106 at rates which place special requirements on the mounting of the first concave mirror 106. In the case of retinal birefringent scanning, the first concave mirror 106 is tilted at an angle of approximately 1.5 degrees (to generate a tilt of approximately 3 degrees), and the first concave mirror 106 is then rotated about the axis of the chief ray of the optical beam.

Unfortunately, the tilt of the first concave mirror 106 can create a problem when it is rotated at high rates. Although the first concave mirror 106 is mechanically balanced when not rotating, the introduction of spin generates forces on the first concave mirror 106 (and the mechanical apparatus holding the mirror) that are not balanced.

For a flat disk, normal spin performed on the flat disk would have forces acting on the mass, but these forces all point away from the center, and have a vector that is normal to the axis of spin. For a mechanically balanced mass (with the center of gravity located precisely on the axis of rotation), the sum of all the force vectors for all divisible portions of the rotating mass cancel, and there is no net force vector.

Figure 2:
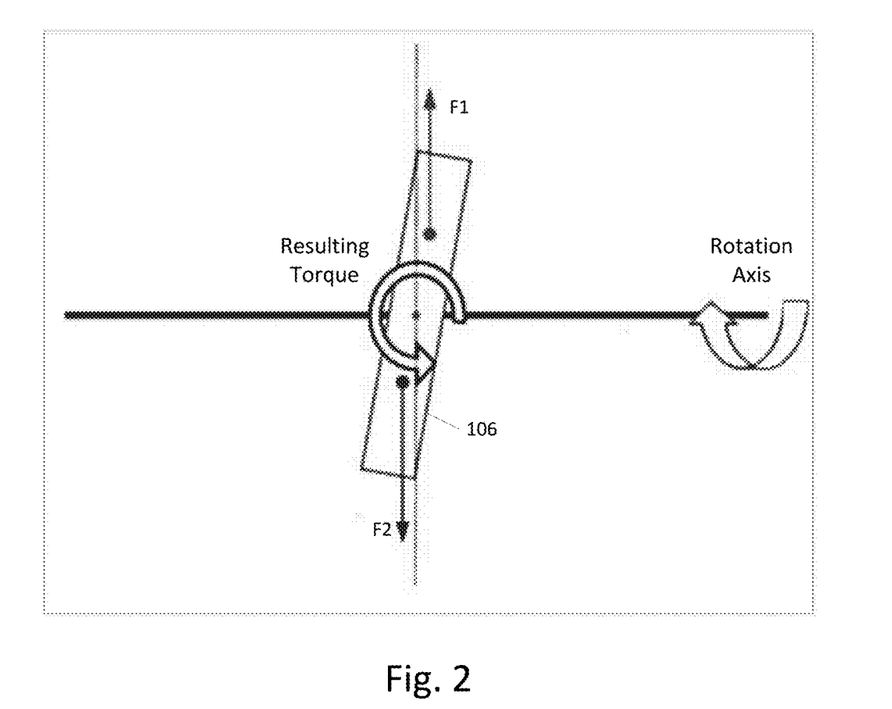
FIG. 2 illustrates the torque exerted on a rotating tilted disk.

However, this is not the case for a tilted mass being rotated about the center of gravity, such as the first concave mirror 106 shown in FIG. 1. FIG. 2 illustrates the torque exerted on the first concave mirror 106. The vertical dotted line separates the upper and lower mass portions of the first concave mirror 106. The dot aligned with the rotation axis indicates the center of gravity of the entire concave mirror 106, the dot above the aligned dot indicates the center of gravity for the upper mass portion of the concave mirror 106 and the dot below the aligned dot indicates the center of gravity for the lower mass portion of the concave mirror 106.

As the tilted mass portions are rotated about the center of gravity, the top half of the mass will have a force vector F1 outward and above the center of gravity, whereas the bottom half of the mass will have a force vector F2 that is outward and below the center of gravity. The result is a speed dependent torque that is exerted onto the concave mirror 106 as the two forces act against each other. Not only is the torque speed dependent (torque increases as speed increases), but it is also continuously oriented parallel to the axis of tilt of the concave mirror 106. Therefore, the torque has a similar mechanical vibration as if there was an off-axis mass.

If the concave mirror 106 is held rigid using a mechanical method, then the torque exerted will perform work and rotate the entire mechanical assembly, if even a small amount. For low speeds, this torque is small and the magnitude of the movement of the entire device which includes the concave mirror 106 is small. But at higher speeds, the torque can become excessively large, and the entire device can vibrate excessively. Such vibration can place undesirable stress on some of the components of the device, possibly leading to fatigue in the components and eventually failure.

Figure 3:
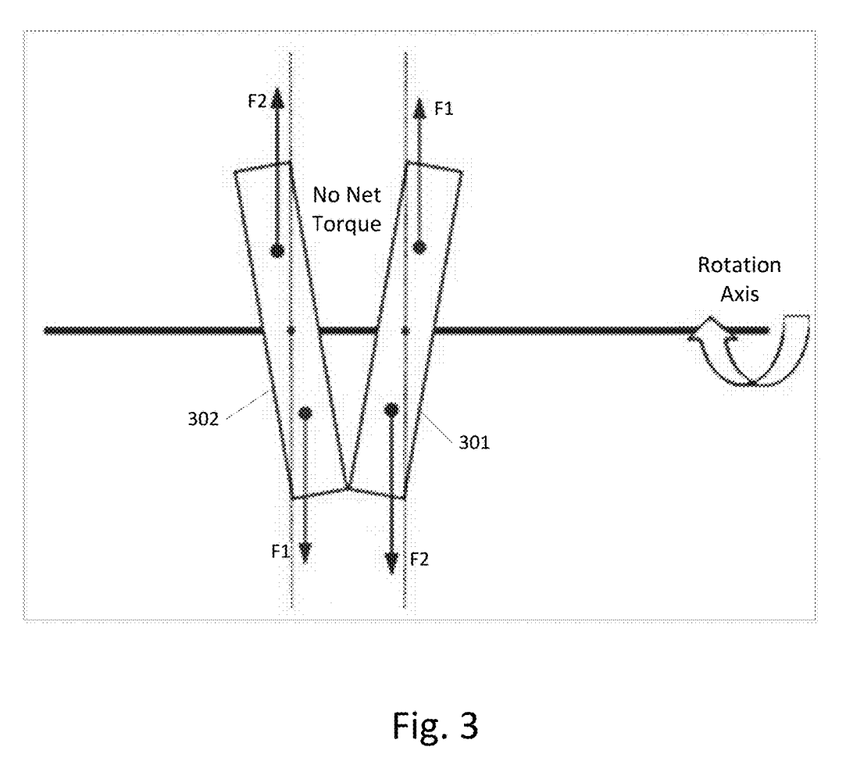
FIG. 3 illustrates a symmetrical disk arrangement used to mitigate torque.

One known approach to minimize excessive vibration with a rotating tilted disk is to use a symmetrical disk which is of the same mass, size and shape of the tilted disk, but angled opposite to the angle of the tilted disk. FIG. 3 illustrates a pair of rotating, tilted disks 301 and 302 which have a symmetric mass and tilt about an imaginary centerline lying between them. The figure would be similar for a pair of rotating, tilted concave mirrors such as those shown in FIG. 1. For the approach shown in FIG. 3, symmetrical disk 302 rigidly attached to disk 301. The assembly of FIG. 3 is constructed such that the overall mass is balanced when there is no rotation. Additionally, due to the symmetrical arrangement of the disks 301 and 302, the torque exerted by the two masses during rotation also cancels out.

There are still potential shortcomings with this approach. Most notable is that the mass of the rotating object has doubled. For a device that performs scanning, this places extra time delay between the time when the motor is started and the time when the needed rotational speed has been achieved. This can make the device unsuitable for stopping and starting, and may require that the device is simply left with the motor spinning so that it is ready to use. Another potential shortcoming with this approach is that the tilted disk may have a shape that is not a simple flat disk but rather a concave disk such as the first concave mirror of the '216 patent. In this situation, a symmetrical concave mirror could be tilted at precisely the same angle (but in an opposite direction) as the first concave mirror. However, the additional component and the additional steps needed to fabricate this arrangement would result in a higher cost for the device. Additionally, there is a lack of machinery which is optimized for fabricating such assemblies and therefore the symmetrical disk approach can involve extra time in manufacturing in addition to the extra materials.

Another potential shortcoming with the symmetrical disk approach is that it can also be complex to resolve or correct for residual errors in manufacturing, which are virtually unavoidable for such an arrangement. Such errors generate vibrations, which need to be corrected. These types of errors are inherently difficult to correct because the assembly needs to be stopped in order to be adjusted, but the motor must be spinning in order to observe the vibration. Furthermore, making the necessary adjustments can be very time consuming.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

The inventors have identified a need for a system which measures fixation and which avoids the mechanical difficulties and torque associated with utilizing a tilted spinning reflector or disk.

Figure 4:
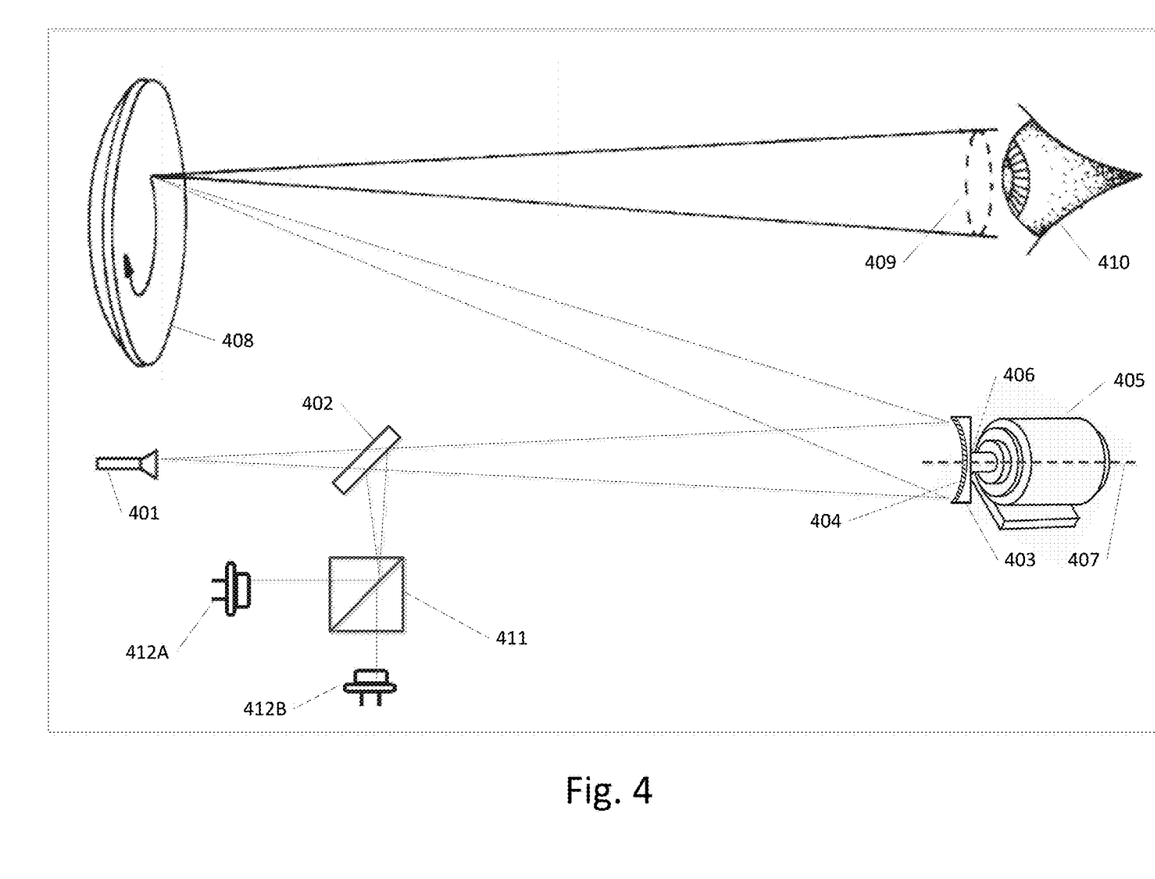
FIG. 4 illustrates an apparatus for fixation measurement according to an exemplary embodiment.

FIG. 4 illustrates an apparatus for fixation measurement according to an exemplary embodiment. The apparatus includes a first reflector 403 which itself includes a diffraction component 404. As will be discussed in greater detail below, the first reflector and the diffraction component can take a variety of forms. For example, the diffraction component can be a diffraction grating superimposed on a concave mirror, a concave Fresnel mirror, a reflection diffraction grating disposed adjacent to a lens, and/or a wedge prism disposed adjacent to a concave mirror.

The first reflector 403 is coupled to a motor 405 via shaft 406 and is configured to rotate about a rotation axis 407. The first reflector 403 reflects light received from a light source 401 onto a second reflector 408 via the diffraction component 404, and reflects light received from the second reflector 408 via the diffraction component 404.

The apparatus also includes one or more photodetectors, such as detectors 412A and 412B, which are configured to capture light which is reflected by the second reflector 408 and subsequently reflected by the first reflector 403.

The second reflector 408 can be configured to reflect light received from the first reflector 403 onto a target area 409 adapted to receive one or more eyes, such as eye 410, of a patient and to reflect light received from the pupil of eye 410 of the patient onto the first reflector 403. The first reflector 403 can then route the light received from the eye 410 of the patient to photodetectors 412A and 412B, which are configured to capture the light which is received from the eye 410 of the patient via the second reflector 408 and then the first reflector 403 as light data.

This light data can include information indicating the fixation of the patient's eye 410. For example, the fixation of the patient's eye 410 can be calculated by a computing device based on one or more polarization-related changes between light emitted by the light source 401 and light received from the patient's eyes 410. For example, a computing device coupled to the apparatus or which receives data from the apparatus can determine polarization-related changes between the incident light and the reflected light, and correlate the polarization-related changes with changes known to occur with known fixation states of the eye. Detection of only one eye fixating, indicating that the other eye is misaligned, is strongly suggestive of the abnormal condition known as strabismus, or misalignment of the eyes.

As shown in FIG. 4, the rotation axis 407 of the first reflector 403 can be a horizontal line. In other words, the slope of the rotation axis 407 can be zero relative to the ground and the rotation axis 407 can be perpendicular to the shaft 406 of motor 405 such that the first reflector has zero tilt relative to the vertical (Y) axis.

The apparatus can also includes one or more beam splitters, such as beam splitters 402 and 411, disposed between photodetectors 412A and 412B and the first reflector 403. The beam splitters can include one or more polarization beam splitters, such as polarized beam splitter 411. Beam splitter 402 is configure to allow the light from the light source 401 to pass through to the first reflector 403 and to route a portion of the light received from the first reflector 403 downwards to polarized beam splitter 411. Polarized beam splitter 411 can then separate the received light and route the separated portions to detectors 412A and 412B.

Unlike the apparatus shown in FIG. 1, the first reflector 403 in the apparatus of FIG. 4 includes a diffraction component 404. The diffraction component 404 in the apparatus of FIG. 4 is a diffraction grating superimposed on the surface of the first reflector 403, which includes a concave mirror. The combination of the diffraction gratings with the concave mirror can be referred to as concave gratings.

By combining the diffraction component 404 with the concave surface of a mirror, a laser waist can be re-imaged to a point off axis from the original. By rotating the concave grating (the reflector 403 including the diffraction component 404) about its axis of symmetry (the rotation axis 407), the re-imaged waist can then sweep out a circle and perform the same function as the first tilted concave mirror in FIG. 1. However, since the concave grating achieves beam tilt using diffraction, the first reflector 403 can be mounted in a vertical orientation and rotated at high speeds without inducing any torque.

Figure 5:
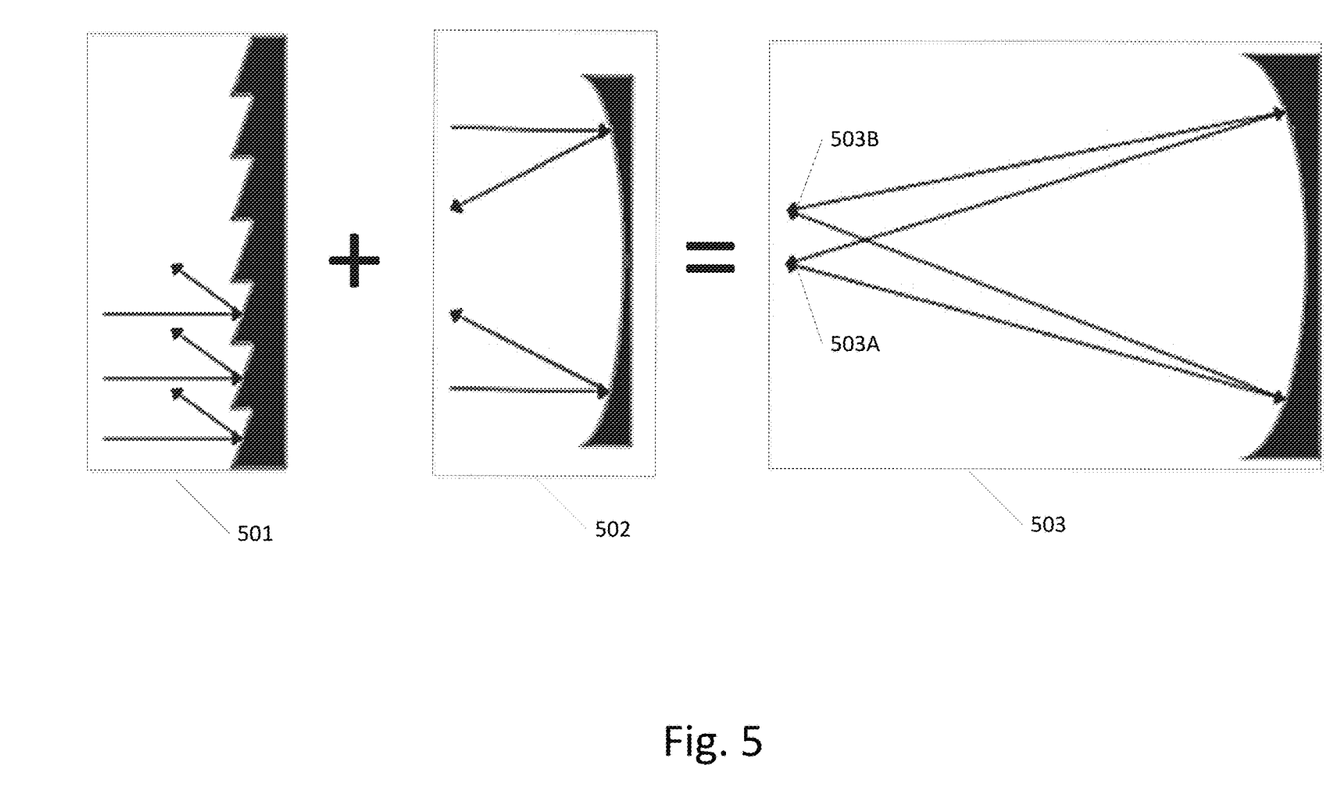
FIG. 5 illustrates a reflector including a diffraction component according to an exemplary embodiment.

As discussed above, the diffraction component 404 can take a variety of forms. FIG. 5 illustrates a reflector including a diffraction component according to an exemplary embodiment. Box 501 illustrates a Fresnel tilted mirror which is a reflective surface with tilted ridges which diffract light and illustrate incident light waves and reflected and diffracted light waves. The surface shown in box 501 can also represent a diffraction grating which diffracts light. The tilted ridges in box 501 are shown greatly magnified and can tilt approximately 25 milliradians (mrads).

Box 502 illustrates a standard non-tilted concave mirror and incident light waves and reflected light waves. Box 503 illustrates the combination of the Fresnel tilted mirror or diffraction grating in box 501 with the non-tilted concave mirror in box 502. The resulting reflector surface in box 503 permits both re-convergence at point 503B of the laser beam from the light source at point 503A as well as the needed beam deviation for retinal birefringence scanning. The ridges are too small to illustrate in box 503 but the effect of the ridges can be seen in the beam deviation of the laser beam reflecting from the reflector surface. The ridges are configured to add to the tilt angle on one side of the reflector surface and subtract from the tilt angle on the opposite side of the reflector surface. Of course, the combined reflector surface shown in box 503 can be a concave mirror with a diffraction grating or a concave Fresnel mirror.

One method involves the use of a diffraction grating (or alternatively a mirrored Fresnel Prism) to achieve this (FIG. 3). The individual gratings 28 and the first concave mirror 24 are shown on the left, and the combination of the two is shown on the right. The combination of the two features into one surface permits both re-convergence of the laser beam as well as the needed beam deviation for retinal birefringence scanning Although not shown for purposes of simplicity, it will be appreciated that according to other embodiments, instead of the apparatus 10 including a combination of the diffraction grating 28 with the first concave mirror 24, the apparatus 10 may include a reflective Fresnel prism combined with the first concave mirror 24 to realize the same functionality.

Figure 6:
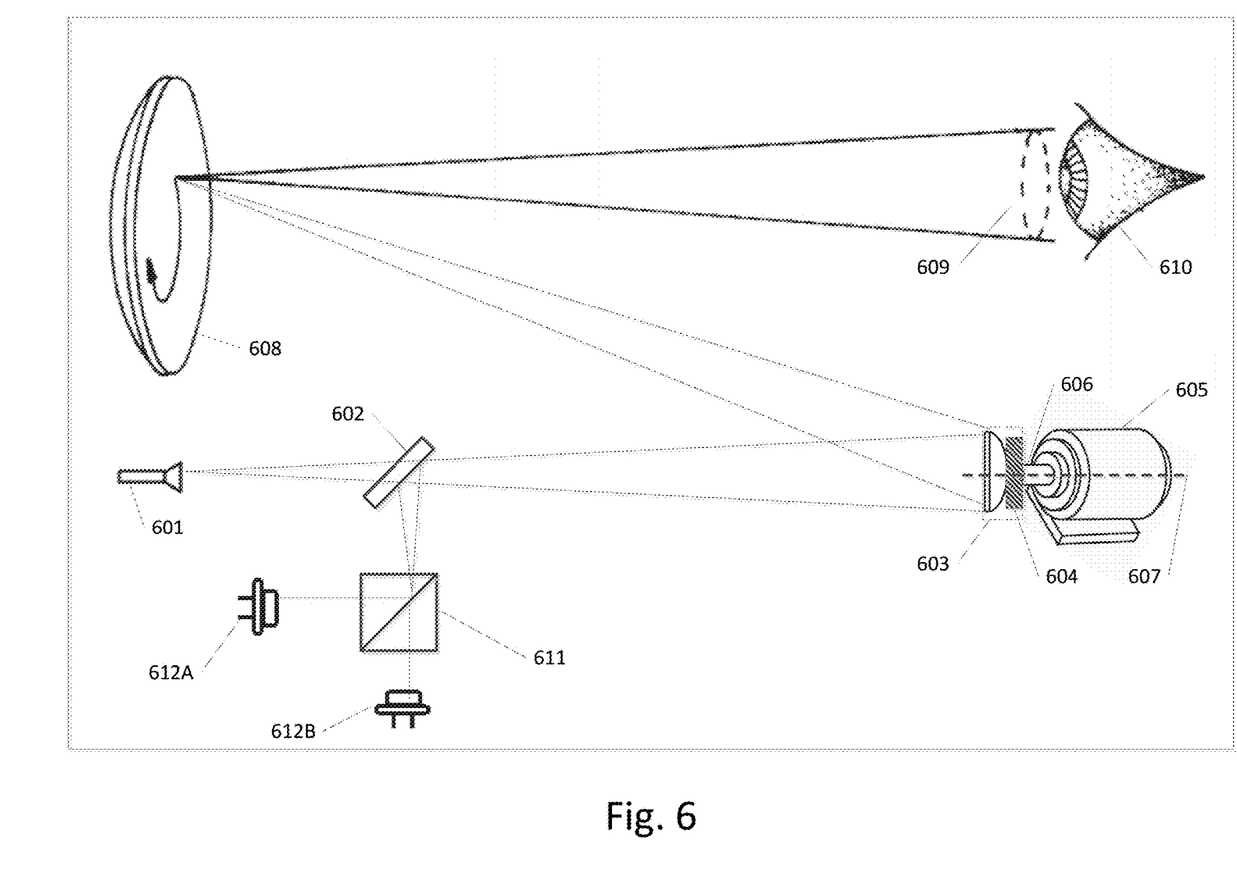
FIG. 6 illustrates another apparatus for fixation measurement according to an exemplary embodiment.

FIG. 6 illustrates another apparatus for fixation measurement according to an exemplary embodiment. The apparatus of FIG. 6 is similar to the apparatus of FIG. 4, with numerals 601, 602, 605, 606, 607, 608, 609, 610, 611, 612A, and 612B in FIG. 6 referencing the same components and features as numerals 401, 402, 405, 406, 407, 408, 409, 410, 411, 412A, and 412B in FIG. 4.

However, unlike the diffraction component 404 of the first reflector 403 in FIG. 4, the diffraction component 604 of the first reflector 603 in FIG. 6 is a reflection diffraction grating and is disposed next to a lens which is also part of the first reflector 403. The lens can be a plano-convex lens spaced a small distance from the reflection diffraction grating. The lens provides the re-shaping of the beam to allow re-imaging the waist, while the reflection diffraction grating provides the beam deviance. Again, as is the case with the concave grating, the entire assembly is mechanically spun about the natural axis of symmetry (rotation axis 607) of the individual components, so no speed induced torque is generated.

Figure 7:
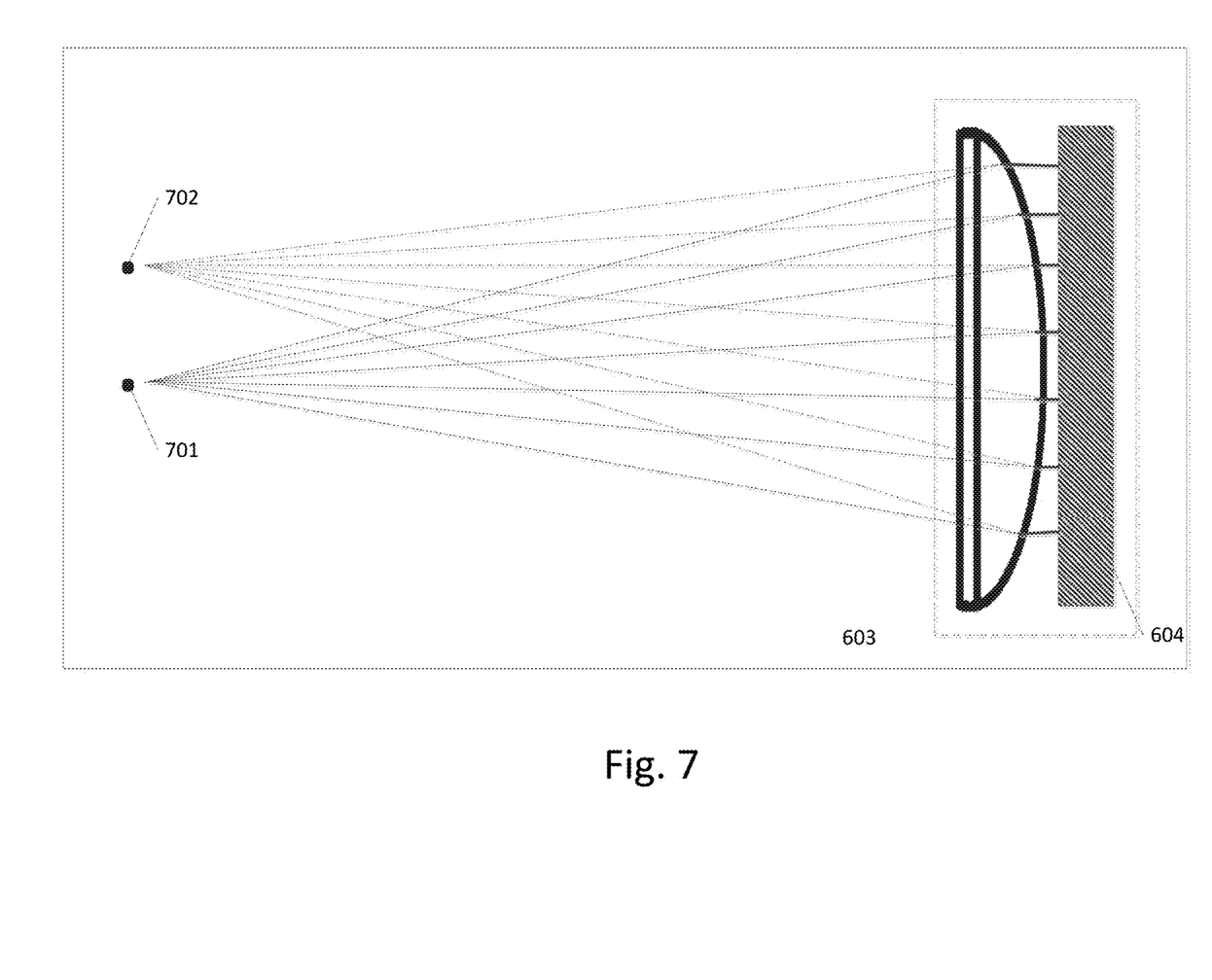
FIG. 7 illustrates a reflector including a lens and a reflection diffraction grating according to an exemplary embodiment.

FIG. 7 illustrates the first reflector 603 of FIG. 6, including the lens and the diffraction component 604, which is a reflection diffraction grating. In FIG. 7, a ray bundle starts from the left at point 701, diverges until hitting the lens, and then hits the reflection diffraction grating. Due to the reflection diffraction grating, the return path rays are off-axis by an angle equivalent to the needed angular deviation for retinal birefringence scanning and converge at point 701.

Figure 8:
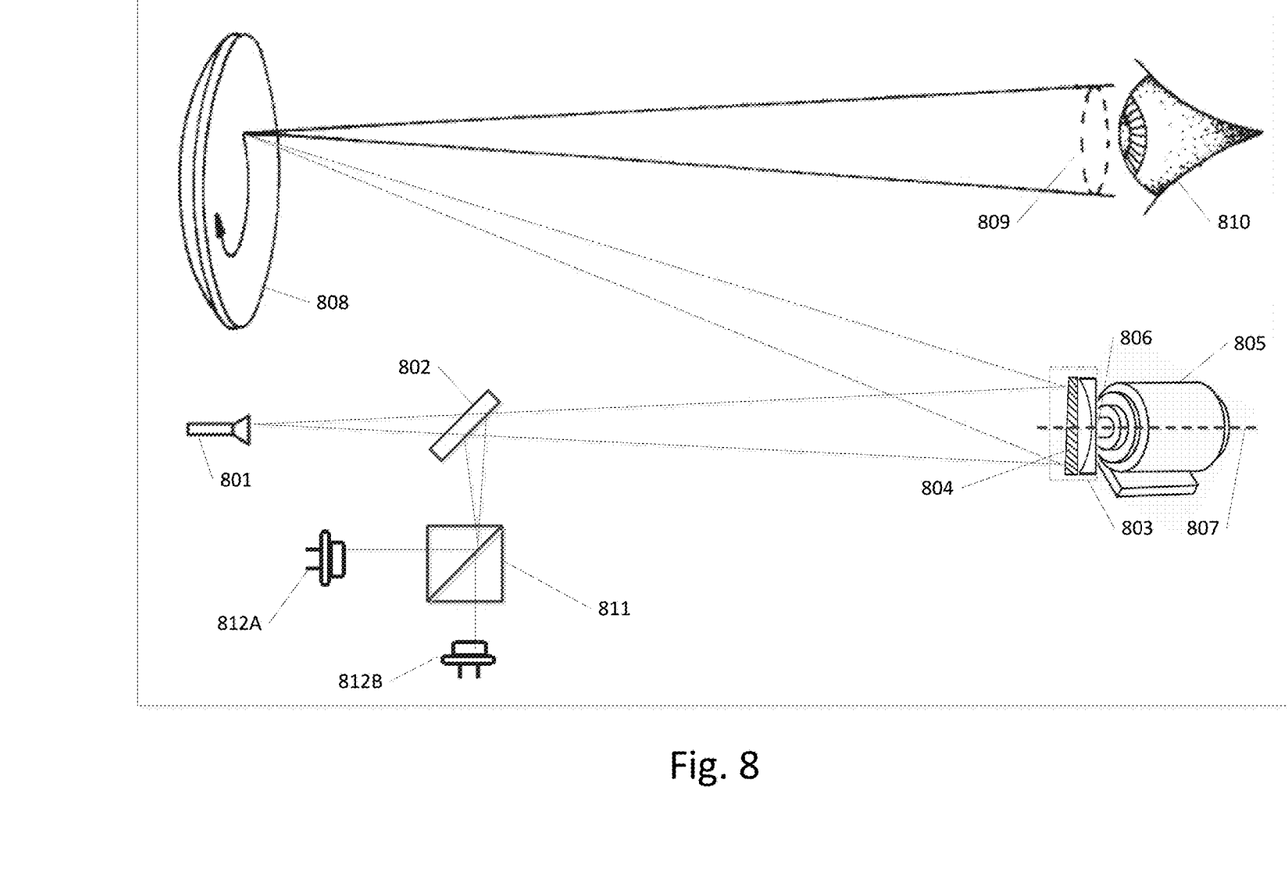
FIG. 8 illustrates another apparatus for fixation measurement according to an exemplary embodiment.

FIG. 8 illustrates another apparatus for fixation measurement according to an exemplary embodiment. The apparatus of FIG. 8 is similar to the apparatus of FIG. 4, with numerals 801, 802, 805, 806, 807, 808, 809, 810, 811, 812A, and 812B in FIG. 8 referencing the same components and features as numerals 401, 402, 405, 406, 407, 408, 409, 410, 411, 412A, and 412B in FIG. 4.

However, unlike the diffraction component 404 of the first reflector 403 in FIG. 4, the diffraction component 804 of the first reflector 803 in FIG. 8 is a wedge prism which is positioned just above/in front of a concave mirror which is also part of the first reflector 803. The wedge prism generates the needed angular deviance for the re-imaged beam waist. The apparatus of FIG. 8 achieves a functionality similar to the symmetric disk arrangement described with regard to FIG. 3, achieves it with a greatly reduced mass, and is easier to balance than devices which utilize a tilted spinning mirror.

In the apparatus of FIG. 8, the mass of the first reflector 803 is already symmetric about the center of mass (when an appropriate symmetric wedge prism is used), so there will be no speed-dependent torque exerted in excess of the usual off-centered mass. However, the off-centered mass can be more easily balanced than a symmetric disk approach. For example, with an appropriate design for a spacer to hold the wedge prism at the correct distance from the concave mirror, the center of mass of the space can be equally yet oppositely off-center from the axis of rotation and thereby achieve mass balance (placing the center of gravity of the entire assembly on the axis of rotation 807).

Figure 9:
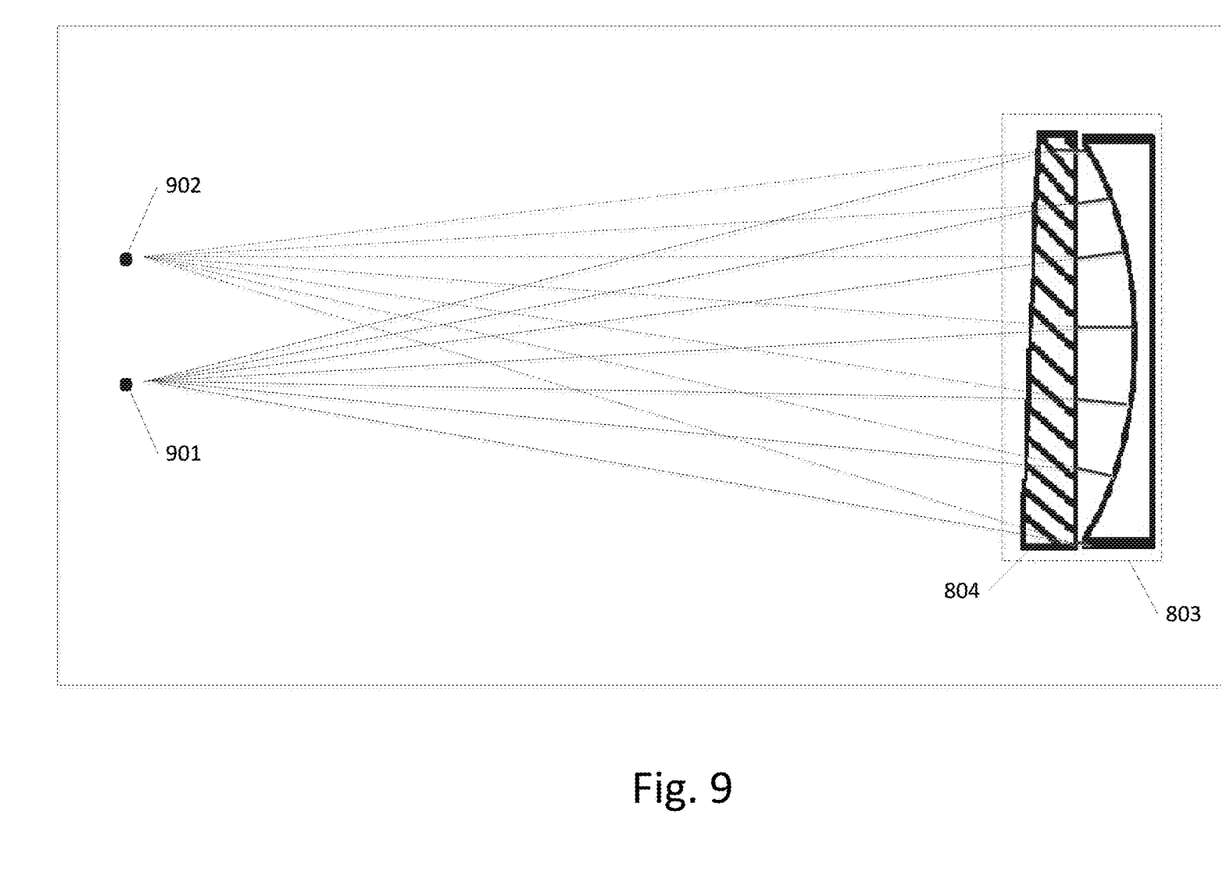
FIG. 9 illustrates a reflector including a prism and concave mirror according to an exemplary embodiment.

FIG. 9 illustrates the first reflector 803 of FIG. 8, including the concave mirror and the diffraction component 804, which is a prism wedge. In FIG. 9, a ray bundle starts from the left at point 901, diverges until hitting the wedge prism, then hits the surface of the first concave mirror, reflects and converges at point 902.

Figure 10:
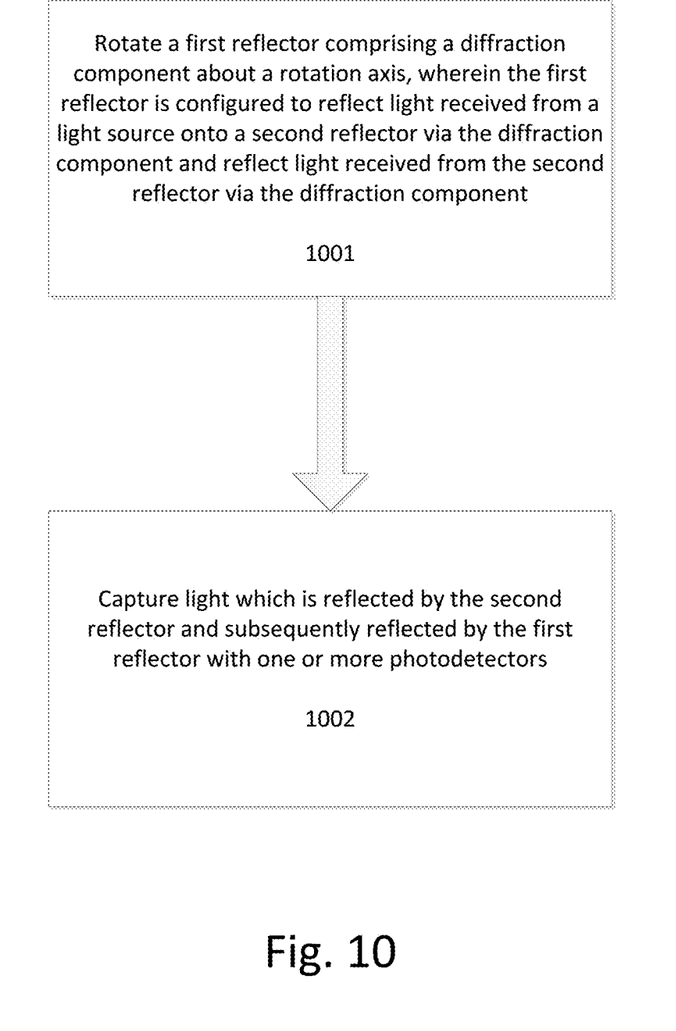
FIG. 10 illustrates a flowchart for a method of fixation measurement according to an exemplary embodiment.

FIG. 10 illustrates a flowchart for a method of fixation measurement. At step 1001 a first reflector comprising a diffraction component is rotated about a rotation axis. The rotation axis can be a horizontal line (having zero slope) so that the first reflector is not tilted. The first reflector is configured to reflect light received from a light source onto a second reflector via the diffraction component and reflect light received from the second reflector via the diffraction component. At step 1002 light which is reflected by the second reflector and subsequently reflected by the first reflector is captured with one or more photodetectors.

The diffraction component can be one or more of a diffraction grating superimposed on a concave mirror, a concave Fresnel mirror, a reflection diffraction grating disposed adjacent to a lens, and/or a wedge prism disposed adjacent to a concave mirror.

The second reflector can be configured to reflect light received from the first reflector onto a target area adapted to receive one or more eyes of a patient and to reflect light received from the one or more eyes of the patient onto the first reflector. Additionally, the one or more photodetectors can be configured to capture the light received from the one or more eyes of the patient via the second reflector and the first reflector as light data. The light data includes information indicating fixation of the one or more eyes. The method can include calculating, by a computing device, the fixation of the one or more eyes based on one or more polarization-related changes between light emitted by the light source and light received from the one or more eyes of the patient. Detection of only one eye fixating, indicating that the other eye is misaligned, is strongly suggestive of the abnormal condition known as strabismus, or misalignment of the eyes.

The light which is reflected by the second reflector and subsequently reflected by the first reflector can pass through one or more beam splitters disposed between the one or more photodetectors and the first reflector prior to capture by the one or more photodetectors. Additionally, the one or more beam splitters can include a polarization beam splitter.

Figure 11:
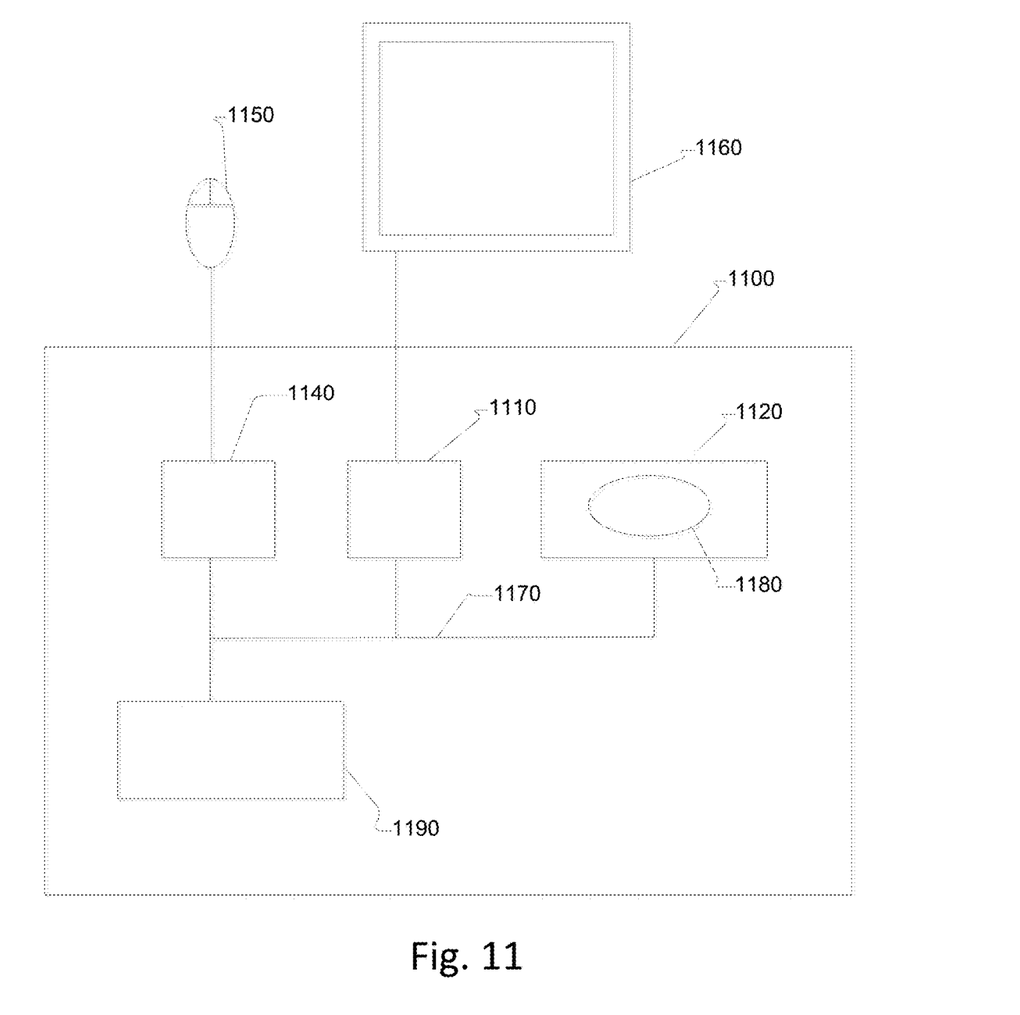
FIG. 11 illustrates an exemplary computing environment that can be used to carry out at least part of the method disclosed herein.

One or more of the above-described techniques can be implemented in or involve one or more computer systems. FIG. 11 illustrates a generalized example of a computing environment 1100. The computing environment 1100 is not intended to suggest any limitation as to scope of use or functionality of a described embodiment.

With reference to FIG. 11, the computing environment 1100 includes at least one processing unit 1110 and memory 1120. The processing unit 1110 executes computer-executable instructions and may be a real or a virtual processor. In a multi-processing system, multiple processing units execute computer-executable instructions to increase processing power. The memory 1120 may be volatile memory (e.g., registers, cache, RAM), non-volatile memory (e.g., ROM, EEPROM, flash memory, etc.), or some combination of the two. The memory 1120 may store software instructions 1180 for implementing the described techniques when executed by one or more processors. Memory 1120 can be one memory device or multiple memory devices.

A computing environment may have additional features. For example, the computing environment 1100 includes storage 1140, one or more input devices 1150, one or more output devices 1160, and one or more communication connections 1190. An interconnection mechanism 1170, such as a bus, controller, or network interconnects the components of the computing environment 1100. Typically, operating system software or firmware (not shown) provides an operating environment for other software executing in the computing environment 1100, and coordinates activities of the components of the computing environment 1100.

The storage 1140 may be removable or non-removable, and includes magnetic disks, magnetic tapes or cassettes, CD-ROMs, CD-RWs, DVDs, or any other medium which can be used to store information and which can be accessed within the computing environment 1100. The storage 1140 may store instructions for the software 1180.

The input device(s) 1150 may be a touch input device such as a keyboard, mouse, pen, trackball, touch screen, or game controller, a voice input device, a scanning device, a digital camera, remote control, or another device that provides input to the computing environment 1100. The output device(s) 1160 may be a display, television, monitor, printer, speaker, or another device that provides output from the computing environment 1100.

The communication connection(s) 1190 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of computer-readable media. Computer-readable media are any available media that can be accessed within a computing environment. By way of example, and not limitation, within the computing environment 1100, computer-readable media include memory 1120, storage 1140, communication media, and combinations of any of the above.

Of course, FIG. 11 illustrates computing environment 1100, display device 1160, and input device 1150 as separate devices for ease of identification only. Computing environment 1100, display device 1160, and input device 1150 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). Computing environment 1100 may be a set-top box, mobile device, personal computer, or one or more servers, for example a farm of networked servers, a clustered server environment, or a cloud network of computing devices.

Having described and illustrated the principles of our invention with reference to the described embodiment, it will be recognized that the described embodiment can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiment shown in software may be implemented in hardware and vice versa.

What is claimed is:

1. An apparatus for fixation measurement, the apparatus comprising:
    a first reflector comprising a diffraction component, wherein the first reflector is configured to rotate about a rotation axis, reflect light received from a light source onto a second reflector via the diffraction component, and reflect light received from the second reflector via the diffraction component; and
    one or more photodetectors configured to capture light which is reflected by the second reflector and subsequently reflected by the first reflector;
    wherein a combination of a reflective component in the first reflector and the diffractive component in the first reflector is configured to rotate and re-image a waist of the light received from the light source onto the second reflector without inducing torque.

2. The apparatus of claim 1, wherein the second reflector is configured to reflect light received from the first reflector onto a target area adapted to receive one or more eyes of a patient and to reflect light reflected from the one or more eyes of the patient onto the first reflector.

3. The apparatus of claim 2, wherein the light reflected from the one or more eyes of the patient is reflected from one or more retinas of the one or more eyes and wherein the one or more photodetectors are configured to capture the light reflected from one or more retinas of the one or more eyes of the patient via the second reflector and the first reflector as light data and wherein the light data includes information indicating fixation of the one or more eyes.

4. The apparatus of claim 3, wherein the fixation of the one or more eyes is calculated based on one or more polarization-related changes between light emitted by the light source and the light reflected from the one or more retinas of the one or more eyes of the patient.

5. The apparatus of claim 1, wherein a center of mass of the first reflector lies on the rotation axis.

6. The apparatus of claim 1, wherein the diffraction component comprises one of: a diffraction grating superimposed on a concave mirror, a concave Fresnel mirror, a reflection diffraction grating disposed adjacent to a lens, and a wedge prism disposed adjacent to a concave mirror.

7. The apparatus of claim 1, further comprising one or more beam splitters disposed between the one or more photodetectors and the first reflector.

8. The apparatus of claim 7, wherein the one or more beam splitters include a polarization beam splitter.

9. A method for fixation measurement, the method comprising:
rotating a first reflector comprising a diffraction component about a rotation axis, wherein the first reflector is configured to reflect light received from a light source onto a second reflector via the diffraction component and reflect light received from the second reflector via the diffraction component; and
capturing light which is reflected by the second reflector and subsequently reflected by the first reflector with one or more photodetectors;
wherein a combination of a reflective component in the first reflector and the diffractive component in the first reflector is configured to rotate and re-image a waist of the light received from the light source onto the second reflector without inducing torque.

10. The method of claim 9, wherein the second reflector is configured to reflect light received from the first reflector onto a target area adapted to receive one or more eyes of a patient and to reflect light reflected from the one or more eyes of the patient onto the first reflector.

11. The method of claim 10, wherein the light reflected from the one or more eyes of the patient is reflected from one or more retinas of the one or more eyes and wherein the one or more photodetectors are configured to capture the light reflected from one or more retinas of the one or more eyes of the patient via the second reflector and the first reflector as light data and wherein the light data includes information indicating fixation of the one or more eyes.

12. The method of claim 11, wherein the fixation of the one or more eyes is calculated based on one or more polarization-related changes between light emitted by the light source and the light reflected from the one or more retinas of the one or more eyes of the patient.

13. The method of claim 9, wherein a center of mass of the first reflector lies on the rotation axis.

14. The method of claim 9, wherein the diffraction component comprises one of: a diffraction grating superimposed on a concave mirror, a concave Fresnel mirror, a reflection diffraction grating disposed adjacent to a lens, and a wedge prism disposed adjacent to a concave mirror.

15. The method of claim 9, wherein the light which is reflected by the second reflector and subsequently reflected by the first reflector passes through one or more beam splitters disposed between the one or more photodetectors and the first reflector prior to capture by the one or more photodetectors.

16. The method of claim 15, wherein the one or more beam splitters include a polarization beam splitter.

17. The apparatus of claim 1, wherein the waist is re-imaged to an area on the second reflector that is dependent on a degree of rotation of the first reflector about the rotation axis and wherein a full rotation of the first reflector about the rotation axis results in the waist being re-imaged to a plurality of areas on the second reflector, the plurality of areas forming a circle.

18. The apparatus of claim 3, wherein the light data includes information indicating fixation of two eyes of the patient and wherein a misalignment in the fixation of the two eyes corresponds to strabismus.

19. The method of claim 9, wherein the waist is re-imaged to an area on the second reflector that is dependent on a degree of rotation of the first reflector about the rotation axis and wherein a full rotation of the first reflector about the rotation axis results in the waist being re-imaged to a plurality of areas on the second reflector, the plurality of areas forming a circle.

20. The method of claim 11, wherein the light data includes information indicating fixation of two eyes of the patient and wherein a misalignment in the fixation of the two eyes corresponds to strabismus.

* * * * *